United States Patent
Harding et al.

(10) Patent No.: US 7,545,910 B2
(45) Date of Patent: Jun. 9, 2009

(54) METHOD AND IMAGING SYSTEM FOR IMAGING THE SPATIAL DISTRIBUTION OF AN X-RAY FLUORESCENCE MARKER

(75) Inventors: Geoffrey Harding, Hamburg (DE); Jens-Peter Schlomka, Hamburg (DE); Gerhard Martens, Henstedt-Ulzburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 214 days.

(21) Appl. No.: 10/547,588

(22) PCT Filed: Mar. 2, 2004

(86) PCT No.: PCT/IB2004/000543

§ 371 (c)(1),
(2), (4) Date: Sep. 1, 2005

(87) PCT Pub. No.: WO2004/078043

PCT Pub. Date: Sep. 16, 2004

(65) Prior Publication Data

US 2006/0182217 A1  Aug. 17, 2006

(30) Foreign Application Priority Data

Mar. 7, 2003 (EP) .................................. 03100561

(51) Int. Cl.
*G01N 23/223* (2006.01)
(52) U.S. Cl. .................... 378/44; 378/4; 378/6; 378/62
(58) Field of Classification Search .............. 378/4–20, 378/44–49, 64, 65, 62
See application file for complete search history.

(56) References Cited

U.S. PATENT DOCUMENTS

| | | | | |
|---|---|---|---|---|
| 3,927,318 A | * | 12/1975 | Macovski | ....................... 378/6 |
| 4,179,100 A | * | 12/1979 | Sashin et al. | ........... 250/370.09 |
| 4,228,353 A | | 10/1980 | Johnson | |
| 6,640,123 B2 | * | 10/2003 | Warne et al. | ................. 600/407 |

OTHER PUBLICATIONS

Q.Yu et al.: "Preliminary experiment of fluorescent X-ray computed tomography to detect dual agents for biological study", J. Synchrotron Rad. (2001), pp. 1030-1034.

Takeda et al, "Fluorescent Scanning X-ray Tomography with Synchrotron Radiation", Rev. Sci. Instrum. 66, Feb. 1995, pp. 1471-1473.

Takeda et al, "Human Thyroid Specimen Imaging by Fluorescent X-Ray computed Tomography with Synchrotron Radiation", SPIE, vol. 3772, Jul. 1999, pp. 258-267.

* cited by examiner

*Primary Examiner*—Jurie Yun

(57) ABSTRACT

The invention describes a method of generating metabolic images of an investigation region (3) of a body (1) by irradiating an X-ray fluorescence marker in that region and detecting the resulting X-ray fluorescence with a fluorescence detector (30). A fan beam (12) is used as a source of primary X-radiation, thus allowing the scanning of a whole body slice (3) in one step. The fluorescence image may be directly measured, e.g. by mapping voxels (104) of the investigation region onto pixels (134) of the detector (130) with the help of a pinhole collimator (132), or it may be reconstructed by procedures of computed tomography. Moreover, a morphological image may be generated by simultaneously recording X-ray transmission through the body (1).

25 Claims, 1 Drawing Sheet

METHOD AND IMAGING SYSTEM FOR IMAGING THE SPATIAL DISTRIBUTION OF AN X-RAY FLUORESCENCE MARKER

The invention relates to an imaging system and a method for imaging the spatial distribution of an X-ray fluorescence marker in an investigation region of an object.

Fluorescent X-radiation is induced by transition of atomic-orbital electrons from high to low energy states after the excitation of inner orbital electrons by primary X-ray photons. The emitted X-ray energy spectrum is characteristic of the excited element, and the intensity of spectral lines is proportional to the content of the element in the sample. In literature a system and a method are described that make use of X-ray fluorescence for imaging the distribution of two fluorescence markers in a phantom (Q. Yu et al.: "Preliminary experiment of fluorescent X-ray computed tomography to detect dual agents for biological study", J. Synchrotron Rad. (2001), pages 1030-1034). The phantom is irradiated with a pencil beam of X-rays from a synchrotron, and the stimulated fluorescence along the beam is measured by a fluorescence detector at right angles to the beam. By shifting and rotating it, the sample can be completely scanned with the pencil beam in a procedure that lasts several hours, and the spatial distribution of the fluorescence marker can be reconstructed from the measured line integrals of fluorescence. Moreover, X-radiation transmitted through the sample is recorded by a transmission detector and used to reconstruct a morphological image of the sample with methods of computer tomography.

Based on this situation, it was an object of the present invention to provide means for imaging the distribution of an fluorescence marker in an object which may particularly be used in medicine for the investigation of patients.

This object is achieved by an imaging system according to claim 1 and a method according to claim 21. Preferred embodiments are disclosed in the dependent claims.

The imaging system according to the present invention is used for imaging the spatial distribution of at least one X-ray fluorescence marker in an investigation region of an object. The object may particularly be a patient, and the marker may be a pharmaceutical that contains an atom with high atomic number (typically between 50 and 79) and that is distributed in the body according to physiological features and/or metabolic processes. The imaging system comprises the following components:

An X-ray source for generating a fan beam that is large enough to irradiate the whole investigation region and that can stimulate fluorescence of the marker. In order to generate fluorescence, the energy of the X-ray quanta must be equal to or higher than the K edge of the fluorescent atom in the marker. The fan beam typically has a thickness from about 1 mm to about 20 mm, and the angle of divergence preferably ranges from about 15° to about 90°, most preferably from about 20° to about 50°.

A fluorescence detector (in the following often simply called "the detector") with at least one sensor region for measuring fluorescence radiation from said marker. The "sensor region" is a sensitive area of the detector, the dimension and shape of which can vary widely according to the special design of the imaging system.

A collimator that lets only radiation from a subarea of the investigation region pass to said at least one sensor region. With other words, the collimator provides for a unique mapping of subareas of the investigation region to sensor regions of the detector. The signal of each sensor region therefore corresponds to the fluorescence intensity in a related subarea of the investigation region.

An image processing unit, for example a microcomputer coupled to the components listed above, for evaluating the measurements of said detector. The algorithms that must be executed by said processing unit depend on the special design of the whole imaging system, and examples for them will be discussed together with preferred embodiments of the invention.

The imaging system described above is particularly suited for medical applications because the fan beam that is used allows it to irradiate a whole two-dimensional investigation region in one step. Therefore, the distribution of one or more X-ray markers can be mapped within a time that is short enough for an application in medicine. In contrast to this, the imaging of fluorescence markers with a pencil beam from a synchrotron typically takes several hours, which prevents the application of this method to the investigation of a patient. Moreover, metabolism is a dynamic process which does not show stationary conditions for such a long time.

Preferably the detector of the system comprises a plurality of sensor regions (i.e. at least two sensor regions), wherein each of these sensor regions corresponds to a different subarea of the investigation region. All of the sensor regions may be identical or similar in shape. By the provision of multiple sensor regions in the detector, a larger area of the investigation region can be measured in one step, which shortens the time to gain the whole spatial distribution of the fluorescence marker accordingly. Preferably, the subareas that are seen by all sensor regions of the detector cover the whole investigation region.

According to another embodiment of the imaging system, the detector and/or the collimator are movable in order to be able to scan the whole investigation region. This embodiment is particularly needed if the whole investigation region is not seen by the detector at one time. In this case, the subareas that can be monitored by the detector must be moved across the investigation region in order to completely scan it.

According to a first main principle of generating an image of the investigation region, the subarea that is seen by the at least one sensor region of the detector corresponds to a voxel of the investigation region. A "voxel" is as usually defined as the smallest volume element of the object that shall be mapped (resolved) by the imaging system and typically has a volume ranging from about 10 mm$^3$ to about 1000 mm$^3$ in the present case. As the signal of the corresponding sensor region directly represents the intensity of fluorescence in the voxel, no laborious reconstruction processes are needed in order to map the fluorescence marker in said voxel.

In a preferred embodiment the detector comprises a two-dimensional array of sensor pixels. The term "pixel" shall denote a sensor area that corresponds to a point of an image, i.e. the smallest unit of the image according to the prevailing resolution. A pixellated detector area particularly allows for a direct point-to-point mapping of the investigation region.

A collimator that may especially be used with the aforementioned pixellated detector comprises one aperture through which the investigation region can be mapped onto the detector area according to the principle of a pinhole camera. Besides a simple design, one advantage of such an imaging system is that the magnification can simply be altered by the relative positions of investigation region, collimator, and detector.

An alternative design of a collimator that is particularly suited for the use with a pixellated detector is that of an array of parallel open channels. Such a multi-channel collimator transmits only X-rays from the investigation region that are parallel to the channels and therefore parallel to each other.

Such a collimator is suited for a point-to-point mapping of the investigation region to the detector area with parallel lines of sight.

According a second main principle of generating an image of the investigation region, the subarea that is seen by the at least one sensor region of the detector has the form of a line that passes through the investigation region. In this case, the term "line" is of course not meant in a strictly mathematical sense but rather denotes an area with a longitudinal extension that is much larger than its extension in a transverse direction. A sensor region that corresponds to said linear subarea measures the fluorescence in the investigation region along a line integral much same way as transmitted X-rays measure the absorption coefficients along a line integral through the body.

According to a preferred embodiment that may particularly be used with a linear subarea as described above, the processing unit is adapted to reconstruct the fluorescence in at least one voxel (preferably in all voxels) of the investigation region from different line integrals of fluorescence, wherein the line integrals shall contain said voxel. Whereas the fluorescence in a voxel cannot be determined from one line integral that contains said voxel, it may be reconstructed if several of such line integrals are available. The underlying problem and its solution are similar to the reconstruction of X-ray transmission images in computed tomography. Computed tomography is the general process of creating cross-sectional or tomographic images from projections, i.e. line integrals, of the object at multiple angles and using a computer for image reconstruction.

The detector and/or the collimator are preferably rotatable about an axis through the investigation region. In the case of the reconstruction of images from line integrals, the axis of rotation is preferably perpendicular to the investigation region. Rotation can then be used to produce line integrals from different directions through the investigation region. However, rotation of the detector and collimator may also be useful if there is a point-to-point mapping of the investigation region to the detector. In this case, movement of the detector will produce images that are obtained from different viewing angles with respect to the investigation region. Therefore, the fluorescence X-rays that generate said images will have travelled through the object on different paths with different absorption characteristics. The disturbance due to different absorption properties of the object may thus be (partially) compensated.

According to another embodiment of the imaging system, the X-ray source can be rotated around an axis vertical to the fan beam. The investigation region may therefore be irradiated from different directions, which helps to compensate the influence of locally varying absorption properties of the object on the primary radiation.

The primary X-rays from the X-ray source will not only stimulate the desired fluorescence from the marker but also produce a considerable amount of unwanted scattered radiation. This background of scattered radiation is superposed to the fluorescence and therefore conceals the desired signal. In the following, various approaches to improve the signal-to-noise ratio in view of this background radiation are described.

According to a first approach, the detector and the collimator are arranged such that only X-rays with an angle of about 90° or more with respect to the primary rays of the fan beam can reach the detector. In this case the background consist of so-called "backscatter radiation", the energy of which is considerably reduced with respect to radiation in forward directions.

It is also possible to measure the fluorescence under an angle smaller than 90°. In this case a measuring position close to the forward direction (0°) is preferred, particularly of about 1° to 5° (most preferably 1° to 2°) with respect to the primary X-rays, i.e. such that a direct view into the X-ray source will just be avoided. Due to a small cross section of the first order Compton scattering in these directions, the background can be kept small in this case.

According to another approach, the X-ray source is adapted to emit such a spectrum of primary X-rays that detected radiation due to Compton scattering of primary X-rays at the energy of the fluorescence of the marker is sufficiently small in order to prevent concealing of the fluorescence radiation. The spectrum of the X-ray source may for example comprise arbitrary contributions of energies below the fluorescence line of the marker, because the resulting scattered radiation then lies below the energy of fluorescence.

In a preferred embodiment, the X-ray source is adapted to produce monochromatic or quasi-monochromatic radiation.

Moreover, the detector can be adapted to discriminate the energies of the incident X-rays. If for example the spectral distribution of radiation from a voxel of the investigation region can be measured, then the contribution of the desired fluorescence line may be separated from the rest of the radiation. The energy resolution of such a detector typically ranges from about 400 eV to about 3000 eV.

According to a further development of the invention, the imaging system comprises a transmission detector for measuring primary X-radiation from the X-ray source that is transmitted through the object. The transmission detector measures the different absorption properties of the object along line integrals corresponding to the paths of X-rays from the source to the transmission detector. The X-radiation that is used for stimulating fluorescence in the investigation region is therefore simultaneously exploited for generating X-ray projections of the investigation region.

In a further development of the aforementioned system, the X-ray source and the transmission detector are rotatable around and axis through the object that is perpendicular to the fan beam. Moreover, the image processing unit is adapted to reconstruct morphological images of the investigation region from projections measured by the transmission detector. Such a system is able to produce sectional images of the object in the investigation region according to the principles of computed tomography. These images add valuable morphological information about the investigation region to the molecular images gained by the fluorescence detector.

The aforementioned morphological images of the investigation region may be exploited during the process of reconstructing or calculating the spatial distribution of the fluorescence marker in the investigation region. In this case, the image processing unit is adapted to reconstruct the image of the spectral distribution of marker in dependence on the distribution of absorption coefficients within the investigation region, i.e. a morphological image of this region. The distribution of absorption coefficients influences both the primary radiation and the observed fluorescence radiation. A region of the body with a high absorption coefficient may for example reduce the amount of observed fluorescence from this region or regions that lie in its shadow, thus pretending a lower concentration of the fluorescence marker than actually present. In order to avoid such errors, it is useful to know the spatial distribution of absorption coefficients in the object such that the calculation of the fluorescence radiation coming from a voxel can be corrected accordingly. If a transmission detector is present as described above, the morphological image of the investigation region may be gained by this detector simultaneously to the acquisition of the fluorescence data. In cases where fluorescence is (also) observed in a direction perpendicular to the fan beam, a morphological image of the object in this direction is needed, which may for example be produced in advance of the fluorescence image by a CT-system.

According to a further development of the imaging system, this comprises means for the irradiation of body volume for purposes of radiotherapy, i.e. the destruction of malignant cells with high-energy radiation. The imaging of the fluorescence marker may in this case be used in order to locate a structure like a tumour and to control the spatially exact application of the radiotherapy. Moreover, it is known that the markers which are used for fluorescence imaging may assist radiotherapy, too. The irradiation means for radiotherapy may comprise another X-ray source with a particularly suited spectrum of X-rays and shape of the corresponding beam. However, the irradiation source may be identical to the X-ray source that is used for imaging the fluorescence marker, too.

The invention further comprises a method for imaging the spatial distribution of a fluorescence marker in an investigation region of an object, the method comprising the following steps:

a) irradiating the whole investigation region with a fan beam of X-rays that are able to stimulate fluorescence of the marker;

b) measuring fluorescence radiation that originates from the marker in at least one subarea of the investigation region;

c) imaging the distribution of the marker in the investigation region based on the measured fluorescence radiation.

The method comprises in general form the steps that can be executed with an imaging system of the kind described above. Therefore, reference is made to the preceding description for more information on the details, advantages and improvements of that method.

According to a further development of the method, the image of the distribution of the marker is put together from the measurements of the subareas, i.e. there is a direct correspondence between measured subareas and the corresponding image regions. The subareas may in this case particularly be voxels of the investigation region that are mapped to corresponding pixels of the desired image.

According to another embodiment of the method, the image of the distribution of the marker is reconstructed from measurements in linear subareas that intersect the investigation region under different angles. Such a reconstruction may particularly be achieved by the known procedures of computed tomography.

The X-ray source may optionally be rotated about an axis perpendicular to the fan beam in order to reduce the influence of different absorption coefficients in the object.

X-radiation that is transmitted through the object may optionally be measured and be used for a the generation of a morphological image of the investigation region.

These and other aspects of the invention will be apparent from and elucidated with reference to the embodiment(s) described hereinafter.

In the following the invention is described by way of example with the help of the accompanying drawings in which.

The imaging systems shown in the accompanying figures rely on externally activated molecular fluorescence imaging. This imaging is similar to conventional radionuclide imaging except that it employs pharmaceuticals labelled with "heavy" atoms as the marker agent. These atoms are activated through the photoelectric effect by an external photon source and the X-ray fluorescence radiation they emit is imaged onto an energy-resolving detector. Pharmaceuticals such as macroaggregated albumin (M.A.A.), dimercaptosuccinate (DMSA) and methylene diphosphonate (M.D.P.) are often labelled with radioactive species (e.g. $^{99m}$Tc) to render them visible in a radionuclide scan, as these molecules selectively bind to specific organs (bone, kidney and lung, respectively). Similarly, high Z elements (where $50 \leqq Z \leqq 79$) may be integrated into such pharmaceuticals in order to make them applicable for X-ray fluorescence (XRF). X-ray fluorescence offers a sensitivity (minimum detectable level=MDL) of better than 1 part in $10^6$ for the "in vivo" measurement of heavy metals (e.g. Cd, Hg and Pb) in the human body. The idea of the invention is to perform a scan of a patient after injection of a pharmaceutical labelled with a heavy element, and to map the distribution of the pharmaceutical tracer with the aid of the X-ray fluorescence radiation it emits on activation by an externally-produced monochromatic X-ray beam.

Figure 1:
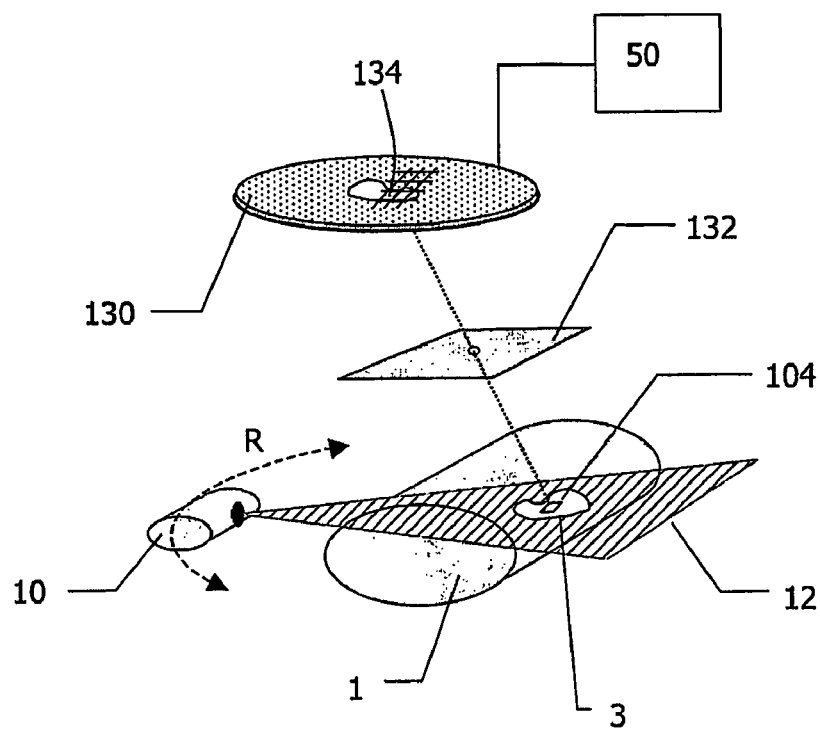
FIG. 1 shows a first embodiment of an imaging system according to the present invention with a point-to-point mapping of an investigation region.

One possible system for performing said fluorescence imaging is shown in FIG. 1. In this example, it is assumed that a pharmaceutical labelled with (non-radioactive) iodine has been injected into the body 1 of a patient. The K absorption edge of iodine lies at 33 keV. It is further assumed that the patient 1 is irradiated with a fan beam 12 of monochromatic radiation, the radiation having an energy slightly above the iodine K edge. An X-ray source 10 (e.g. Fluor'X from Panalytical) equipped with a secondary target of Ce produces a beam with a suitable $K_{\alpha 1}$ line at 34.7 keV. The divergence of the fan beam 12 is such that it irradiates a region with a diameter of at least 50 cm within the body of the patient.

Iodine atoms that are concentrated in region 2 of the body 1 are activated through the photoelectric effect and decay with the emission of fluorescence radiation of energy $\geqq 28.6$ keV ($K_{\alpha 1}$). Above the patient 1 is an energy-resolving detector 130 operating e.g. on the Anger principle or preferably comprising a pixellated semiconductor (e.g. CdZnTe, Si etc.). The energy resolution of Si at these energies is about 400 eV. The two-dimensional sensitive area of the detector 130 is divided into small rectangular pixels 134 (or "sensor regions"), some of which are indicated in the Figure (not to scale). The detector 130 receives only radiation through the aperture (pinhole) of a collimator 132 disposed between the patient 1 and the detector 130 which has the effect of imaging the distribution of the labelled species onto the detector. The processing of the signals from the pixels 134 of the detector 130 is executed by a processing unit 50 (e.g. a workstation). Moreover, the resulting image may be displayed on a monitor (not shown) for inspection by a physician.

The single and multiple Compton scatter arriving at the detector 130 are shifted to lower energy because of the large effective angle of scatter (>90° in FIG. 1). If the detector has sufficient energy resolution to discriminate the XRF signal from the Compton scatter background, it is possible to map the distribution of labelled tracer with virtually no background.

Depending on the characteristics of the marker, the X-ray source, and the system geometry, it may also be preferred to measure the fluorescence of lines other than $K_\alpha$, namely of $K_\beta$. If for example Ce is used as target in the X-ray source, the primary X-radiation has an energy of about 34.7 keV. This energy is shifted to 30.8 keV by Compton scattering under an angle of 150°, which is below the $K_\beta$ line (32.2 keV) but above the $K_\alpha$ line (28.6 keV) of iodide.

In order to minimize self absorption of the primary beam 12 and the XRF radiation in the object it is possible to irradiate the patient 1 from several different directions. This is achieved by rotating the X-ray source 10 around an axis perpendicular to the fan beam 12, as indicated by circle R in FIG. 1.

Figure 2:
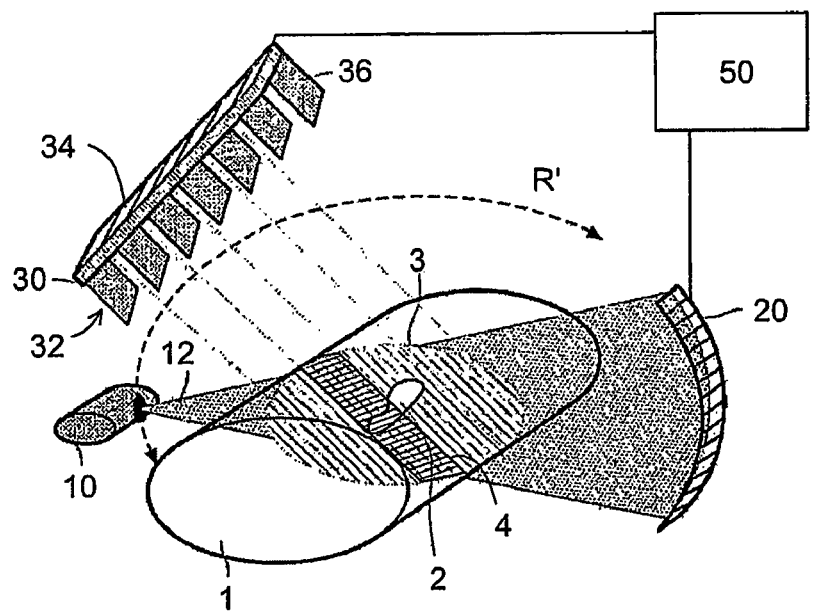
FIG. 2 shows a second embodiment of an imaging system according to the present invention with a reconstruction of the marker distribution in an investigation region.

A greatly improved removal of self-absorption effects can be achieved when the fluorescence imaging is combined with information from volume CT scanning so that the attenuation of both the primary and XRF beams within the patient can be properly accounted for. In the case of FIG. 1, the volume CT may be produced in advance by a conventional CT-system (not shown). In the system of FIG. 2, which will now be described in more detail, the morphological image is produced simultaneously with the molecular imaging of the fluorescence marker.

In FIG. 2, a monochromatic radiation source 10 is again collimated to irradiate a fan beam 12 which may have a thickness of several millimeters (note that this fan beam 12 is perpendicular to the fan beam of FIG. 1). Radiation traversing the body of a patient 1 is incident on a one-dimensional spatial-resolving detector 20 to record the transmission projection. Marker material 2 forming an X-ray fluorescence distribution has been introduced into the body 1. A second one-dimensional detector 30 featuring both spatial and energy resolution is arranged above the patient 1 to monitor the X-ray fluorescence radiation generated by the marker material 2 emitted at a fairly large angle of about 120° with respect to the primary fan beam 12 in order to achieve that the scattered fluorescence radiation is detected with as little Compton-scattered radiation as possible. The relative geometry of the source 10 and both transmission and scatter detectors 20, 30 is fixed. They are rotated relative to a longitudinal axis through the body 1, i.e. an axis perpendicular to the fan beam 12. In this way, a CT slice 3 data set can be measured both with respect to transmission and fluorescence.

The transmission data set is reconstructed for the slices of interest using standard algorithms. Several reconstruction algorithms are known, including filtered back-projection (FBP) and an algebraic reconstruction technique (ART). Now, when morphologic images are generated from the measured attenuation data by a first reconstruction, which for example makes use of the FBP or ART algorithms, a matrix of $\mu$ values (where $\mu$ is the linear attenuation coefficient for X-rays) is obtained which can subsequently be used for reconstructing metabolic images by a second reconstruction procedure. Iterative algorithms are typically preferred for the second reconstruction step as they have the advantage that a-priori information can be incorporated at each step of the reconstruction process to improve the quality of the reconstructed images.

In the system described above the same monochromatic or quasi-monochromatic radiation source 10 is used for activating molecular fluorescence as well as for obtaining morphologic images. Normally, the X-ray beams used in medical imaging are polychromatic with a moderately broad energy spectrum. It is known that a polychromatic X-ray beam becomes more penetrating, or harder, as it traverses through matter. This so-called beam hardening causes artefacts in the morphologic images and requires correction. Beam hardening is avoided with the proposed use of (quasi) monochromatic radiation.

More than one of each detectors 20, 30 can be used to increase the detector area, in particular of detector 30, and thereby giving the opportunity to reduce the applied dose of marker material, the measuring time and/or the dose of primary X-rays.

The fluorescence detector 30 can be placed at a certain distance from the rotation axis, for example 40 cm in the same plane as the fan beam 12 only. A parallel hole secondary collimator of the type used in nuclear imaging, for example SPECT, projects the body slice 3 irradiated by the primary fan beam 12 onto said one-dimensional fluorescence detector 30 which advantageously is a segmented spectroscopic detector. X-ray data falling within an energy window at which the background is low represent line integrals of the X-ray fluorescence along the line of sight of the scatter collimator 32, weighted by the object attenuation which effects both the primary and scatter beam intensities. An attenuation correction can be performed much in the manner of SPECT, as the XRF lines have energy similar to the exciting photons. The linear subarea 4 of the investigation region 3 that is mapped onto one single sensor field 34 of the detector 30 is shown in FIG. 2 with largely exaggerated width.

The collimator 32 is formed of parallel lamella 36 which may have a height of 100 mm. It is assumed that the lamella 36 are spaced 5 mm apart to yield the necessary spatial resolution and that the detector element length perpendicular to the scan plane is 50 mm. The detector element array corresponds to a solid angle subtended at the scatter voxel of $2 \cdot 10^{-3}$ sr. The intrinsic spatial resolution of the detector is assumed to be better than 5 mm×50 mm, and the detector is assumed to have 100% efficiency. To enable good separation of the fluorescence radiation and the inelastic peak due to single and multiple Compton scatter, the detector energy resolution should be better than 3% corresponding to the value obtained with semiconductor detectors such as Ge, CdTe or CZT.

A suitable XRF marker is Gd (Z=64, A=157) which is widely available and routinely used in magnetic resonance imaging. It is desired to use a higher Z marker, as this implies a higher excitation and fluorescence decay energy, thus reducing attenuation effects. If for instance a Fluor'X device mentioned above is used for the X-ray source 10, it can be equipped with a Yb target having $K_{\alpha 1}$ and $K_{\alpha 2}$ slightly higher than the K edge of Gd.

An important advantage of the designs shown in FIGS. 1 and 2 is that they make use of a fan beam 12 which allows for a comparatively fast scanning of the investigation region 3, thus making the system particularly suited for medical applications. Based on this approach, various modifications of the described designs are possible. In this respect, reference is made to the article G. Harding: "Inelastic photon scattering: effects and applications in biomedical science and industry" (Radiat. Phys. Chem. 50, pages 91-111 (1997)) that describes imaging procedures for X-ray scatter.

The fluorescence imaging technique described above has several advantages relative to conventional radionuclide imaging. As the primary beam 12 may be collimated, information is available about the location of the labelled species in the body and 3-D imaging without reconstruction is feasible. Moreover, the spatial and contrast resolution may be improved as a certain target atom has the chance of repeatedly emitting photons into the detector. Further the choice of possible label elements is much greater as it is not necessary to use a radioactive element. Additionally, high Z elements greatly increase treatment efficiency in radiotherapy, when the label is also used for this purpose. Finally, XRF imaging avoids the use of radioactive substances and the associated radiation hazard they pose when they are accumulated in the body.

The invention claimed is:

1. Imaging system for imaging the spatial distribution of an X-ray fluorescence marker in an investigation region of an object, comprising an X-ray source for generating a fan beam that is large enough to irradiate the whole investigation region and that can stimulate fluorescence of the marker; a fluorescence detector with at least one sensor region for directly measuring fluorescence radiation from said marker; a collimator that is adapted to let only radiation from a subarea of the investigation region pass to said sensor region; an image processing unit for evaluating the measurements of said detector, wherein the radiation source, the detector, and the collimator are arranged such that only X-rays having an angle of 90° or more with respect to the rays of the fan beam reach the detector.

2. The imaging system according to claim 1, wherein the detector comprises a plurality of sensor regions, each of them corresponding to a different subarea of the investigation region.

3. The imaging system according to claim 1, wherein the detector and/or the collimator are movable in order to scan the whole investigation region.

4. The imaging system according to claim 1, wherein the subarea corresponds to a voxel of the investigation region.

5. The imaging system according to claim 1, wherein the detector comprises a two-dimensional array of sensor pixels.

6. The imaging system according to claim 1, wherein the collimator comprises one aperture.

7. The imaging system according to claim 1, wherein the collimator comprises an array of parallel open channels.

8. The imaging system according to claim 1, wherein the subarea has the shape of a line that passes through the investigation region.

9. The imaging system according to claim 1, wherein the image processing unit is adapted to reconstruct the fluorescence in at least one voxel of the investigation region from different line integrals of fluorescence which contain said voxel.

10. The imaging system according to claim 1, wherein at least one of the detector and the collimator are rotatable about an axis through the investigation region.

11. The imaging system according to claim 1, wherein the X-ray source is rotatable about an axis perpendicular to the fan beam.

12. The imaging system according to claim 1, wherein the X-ray source emits such a spectrum of primary X-rays that the radiation intensity which (a) is due to Compton scattering, (b) reaches the detector, and (c) has an energy like the fluorescence, is lower than a predetermined threshold of intensity.

13. The imaging system according to claim 1, wherein the X-ray source is monochromatic or quasi-monochromatic.

14. The imaging system according to claim 1, wherein the detector is adapted to discriminate the energy of the incident X-rays.

15. The imaging system according to claim 1, comprising a transmission detector for measuring primary X-radiation from the X-ray source that is transmitted through the object.

16. The imaging system according to claim 15, wherein the X-ray source and the transmission detector are rotatable about an axis perpendicular to the fan beam; the image processing unit is adapted to reconstruct morphological images of the investigation region from projections measured by the transmission detector.

17. The imaging system according to claim 1, wherein the image processing unit is adapted to reconstruct the image of the spatial distribution of the fluorescence marker taking into consideration the distribution of absorption coefficients in the investigation region.

18. The imaging system according to claim 1, wherein it comprises means for the irradiation of a body volume for purposes of radiotherapy.

19. Imaging system for imaging the spatial distribution of an X-ray fluorescence marker in an investigation region of an object, comprising an X-ray source for generating a fan beam that is large enough to irradiate the whole investigation region and that can stimulate fluorescence of the marker; a fluorescence detector with at least one sensor region for directly measuring fluorescence radiation from said marker; a collimator that is adapted to let only radiation from a subarea of the investigation region pass to said sensor region; an image processing unit for evaluating the measurements of said detector, wherein the radiation source, the detector, and the collimator are arranged such that only X-rays having an angle of about 1° to 5° with respect to the X-rays of the fan beam reach the detector.

20. Method for imaging the spatial distribution of an X-ray fluorescence marker in an investigation region of an object, comprising the following acts: positioning a radiation source and a fluorescence radiation detector, such that only X-rays having an angle of 90° or more with respect to the rays of the fan beam reach the fluorescence radiation detector, irradiating with the radiation source, the whole investigation region with a fan beam of X-radiation that is able to stimulate fluorescence of the marker; directly measuring with the fluorescence radiation detector, fluorescence radiation that originates from the marker in at least one subarea of the investigation region; imaging the distribution of the marker in the investigation region based on the measured fluorescence radiation.

21. The method according to claim 20, wherein the image of the distribution is additively composed from measurements of subareas.

22. The method according to claim 20, wherein the image of the distribution is reconstructed from measurements of fluorescence in linear subareas that intersect the investigation region at different angles.

23. The method according to claim 20, wherein the X-ray source is rotated about an axis perpendicular to the fan beam.

24. The method according to claim 20, wherein X-radiation transmitted through the object is measured and used for the generation of a morphological image of the investigation region.

25. Method for imaging the spatial distribution of an X-ray fluorescence marker in an investigation region of an object, the method comprising acts of: positioning a radiation source and a fluorescence radiation detector, such that only X-rays having an angle of about 1° to 5° with respect to the X-rays of the fan beam reach the fluorescence radiation detector; irradiating with the radiation source, the whole investigation region with a fan beam of X-radiation that is able to stimulate fluorescence of the marker; directly measuring with the fluorescence radiation detector, fluorescence radiation that originates from the marker in at least one subarea of the investigation region; imaging the distribution of the marker in the investigation region based on the measured fluorescence radiation.

* * * * *